United States Patent [19]

Charon et al.

[11] Patent Number: 4,530,837
[45] Date of Patent: Jul. 23, 1985

[54] PEPTIDE DERIVATIVES, THEIR PREPARATION PROCESS AND THEIR PHARMACEUTICAL USE

[75] Inventors: Marie-Helene Charon, Paris; Pierre Fromageot, Le Chesnay; Paul P. Van Chuong, Antony, all of France

[73] Assignee: Commissariat a l'Energie Atomique, Paris, France

[21] Appl. No.: 561,785

[22] Filed: Dec. 15, 1983

[30] Foreign Application Priority Data

Dec. 16, 1982 [FR] France ................. 82 21127

[51] Int. Cl.$^3$ ............... A61K 37/00; C07C 103/52
[52] U.S. Cl. ................... 514/18; 260/112.5 R
[58] Field of Search .............. 260/112.5 R; 424/177

[56] References Cited

U.S. PATENT DOCUMENTS 4,012,367  3/1977  Mazur ............... 260/112.5 R
4,164,571  8/1979  Bonfils et al. ......... 260/112.5 R

OTHER PUBLICATIONS

E. Gross, et al., The Peptides, vol. I (1979), pp. 80 & 89.

Primary Examiner—Delbert R. Phillips
Attorney, Agent, or Firm—James E. Nilles

[57] ABSTRACT

The invention relates to novel peptide derivatives, their preparation process and their pharmaceutical use.

These derivatives are in accordance with the following formula:

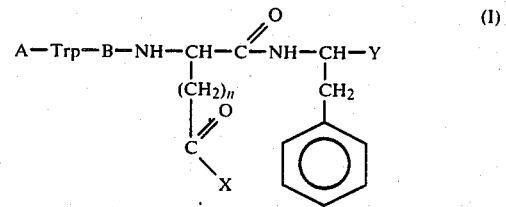

in which A stands for hydrogen, a radical derived from an amino acid, a group of formula DE in which D represents the N-t-butyloxycarbonyl (BOC), tertamyloxycarbonyl (tAOC), N-benzyloxycarbonyl, N-benzoyl, N-acetyl, N-pivaloyl, N-carbamoyl, or N-succinyl radical, and E stands for a single bond or a radical derived from an amino acid which is either not substituted or substituted by $HSO_3$ or a peptide formed from 2 to 5 amino acids, either unsubstituted or substituted by $HSO_3$; B represents the L-methyonyl, D-methionyl, L-norleucyl, D-nodeucyl, L-leucyl, D-leucyl, L-norvalyl or D-norvalvyl radical; Y represents H, $CH_2OH$, $COOR^1$ with $R^1$ representing hydrogen or an allyl radical in $C_1$ and $C_4$ or $CO-NHR^2$ with $R^2$ representing hydrogen, an alkyl radical in $C_1$ and $C_4$ or $NH_2$; m is an integer between 0 and 6 and X represents an amino derivative having at least 5 carbon atoms and a pentagonal unsaturated heterocycle.

They are usable as antagonists of gastrin and histamine.

10 Claims, 8 Drawing Figures

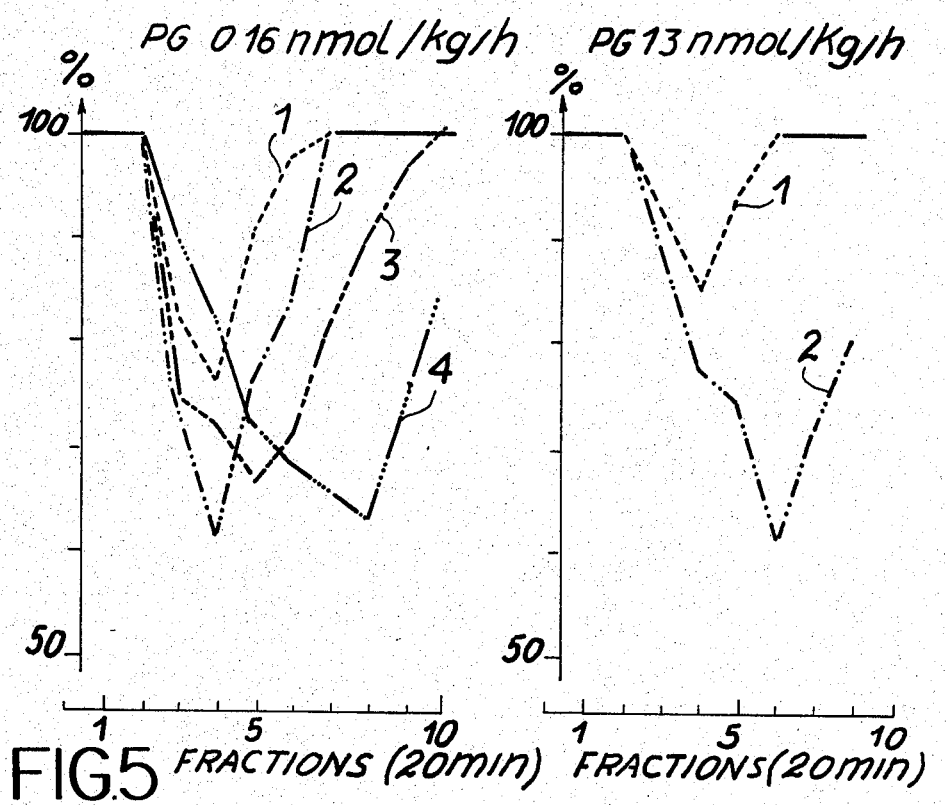
FIG.5
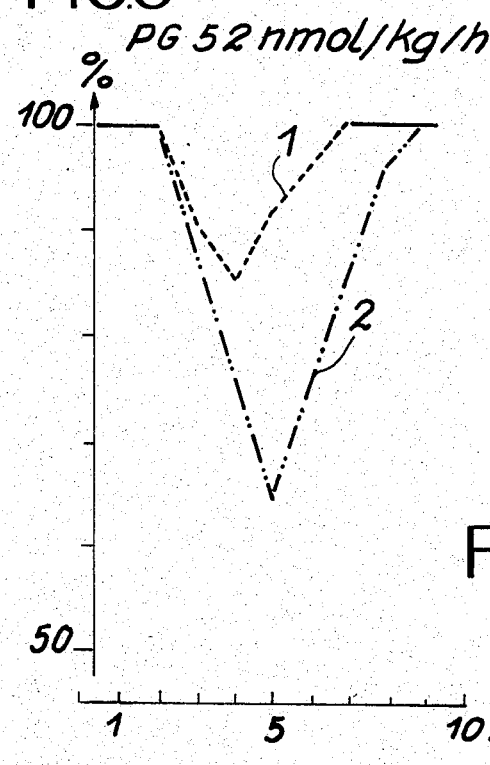
FIG.6
FIG.7

PEPTIDE DERIVATIVES, THEIR PREPARATION PROCESS AND THEIR PHARMACEUTICAL USE

BACKGROUND OF THE INVENTION

The present invention relates to novel peptide derivatives, their preparation process and their pharmaceuticals. More specifically, it relates to peptide derivatives of pentagastrin more particularly usable as antagonists to gastrin and "related polypeptides".

It is pointed out that gastrin is a natural hormone, more particularly known as being responsible for the secretion of gastric juice. Its manner of acting on the organs of the digestive system, like that of most hormones, is linked with the presence in said organs of target cells, whose plasma membranes have specific biological receptors able to fix the hormone molecules and, under the action of the latter, produce a cascade of biochemical reactions leading to the production of a specific product, such as hydrochloric acid.

The term "related polypeptides" is used to describe a group of polypeptides having at their C-terminal end the sequence of four amino acids: L-tryptophanyl-L-methionyl-L-aspartyl-L-phenylalanine amide, characterizing the biological activity of gastrin. These polypeptides are also able to produce biochemical reactions by fixing to specific receptors.

It is known that a hormonal hypersecretion can lead to certain known pathological problems, e.g. for gastrin, during the Zollinger-Ellison syndrome and are also suspected in numerous other ailments.

Over the past few years, research has been directed at the preparation of compounds able to inhibit gastric secretions. To this end, polypeptides have been proposed, which act as antagonists to pentagastrin, such as compounds of formula A-W-X-Asp-Y-NHR, in which A is hydrogen, an alkanoyl group with 2 to 6 carbon atoms, a succinyl group, t-butoxycarbonyl, benzyloxycarbonyl, D-pyroglutamyl or L-pyroglutamyl; W is the tryptophanyl or D-tryptophanyl radical; X is the methionyl, D-methionyl, norleucyl or D-norleucyl radical; Y is a radical of formula:

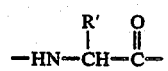

in which R' is an alkyl radical in $C_1$ to $C_6$, or an alkyl or cycloalkyl radical in $C_6$ to $C_7$, or of formula:

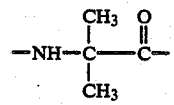

and R is hydrogen or an alkyl radical in $C_1$ to $C_6$.

In these polypeptides, e.g. N-t-butoxycarbonyl-L-tryptophanyl-L-methionyl-L-aspartyl-D-alanine amide the replacement of the L-phenylalanyl radical of the sequence of the four amino acids of gastrin by the radical:

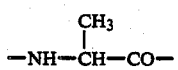

makes it possible to obtain this inhibiting effect (cf U.S. Pat. No. 4,012,367 of Robert H. Mazur).

For the inhibition of gastric secretion, use has also been made of polypeptides having the sequence of the four amino acids of gastrin, but whose tryptophanyl residue has been replaced by the orthonitrophenylthio radical, as described in French Pat. No. 2,364,659, filed on 21.9.1976, in the name of the Commissariat à l'Energie Atomique and INSERM. Thus, hitherto, it has been possible to obtain this gastric secretion inhibiting effect, either by modifying the characteristic sequence of the four amino acids of gastrin, or by substituting the tryptophanyl residue of said sequence.

As a result of further research, it has now been found that an inhibiting effect can also be obtained by modifying the aspartyl residue of the sequence of the four amino acids of gastrin.

SUMMARY OF THE INVENTION

The present invention specifically relates to novel peptide derivatives substantially having the sequence of the four amino acids of gastrin and having a gastric secretion inhibiting effect, as a result of the modification of the aspartyl residue.

The peptide derivative according to the invention complies with the following formula:

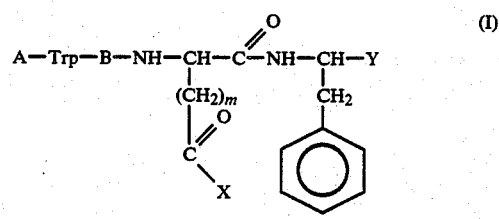

in which A stands for hydrogen, a radical derived from an amino acid, a group of formula DE in which D represents the N-t-butyloxycarbonyl (BOC), tert-amyloxycarbonyl (tAOC), N-benzyloxycarbonyl, N-benzoyl, N-acetyl, N-pivaloyl, N-carbamoyl or N-succinyl radical, and E stands for a single bond or a radical derived from an amino acid which is either not substituted or substituted by $HSO_3$ or a peptide formed from 2 to 5 amino acids, either unsubstituted or substituted by $HSO_3$; B represents the L-methionyl, D-methionyl, L-norleucyl, D-norleucyl, L-leucyl, D-leucyl, L-norvalyl or D-norvalvyl radical; Y represents H, $CH_2OH$, $COOR^1$ with $R^1$ representing hydrogen or an allyl radical in $C_1$ to $C_4$ or $CO-NHR^2$ with $R^2$ representing hydrogen, an alkyl radical in $C_1$ to $C_4$ or $NH_2$; m is an integer between 0 and 6; and X represents a radical of formula:

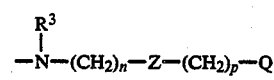

in which n is an integer between 1 and 8, p is an integer between 0 and 3, $R^3$ stands for H or $CH_3$, Z stands for a single bond or S, and Q represents a radical chosen from among the radicals of formula:

in which $R^4$ stands for H or an alkyl radical in $C_1$ to $C_4$,

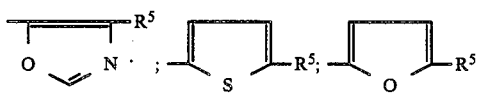

with $R^5$ standing for H, an alkyl radical in $C_1$ to $C_4$, or

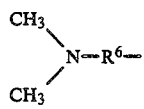

with $R^6$ representing an alkylene radical in $C_1$ to $C_3$; and

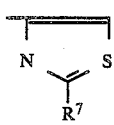

with $R^7$ representing H, an alkyl radical in $C_1$ to $C_4$,

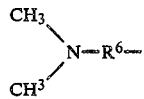

with $R^6$ having the meaning given hereinbefore, or

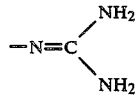

According to the invention, in the group DE, the radicals derived from amino acids which can be used are radicals of D or L-pyroglutamyl, L or D-alanyl, β-alanyl, glycyl, L or D-prolyl, L or D-valyl, L or D-phenylalanyl, L or D-homocysteyl, L or D-aspartyl, L or D-glutamyl, L or D-histidyl, L or D-methionyl, L or D-threonyl, L or D-seryl, L or D-cysteyl, L or D-leucyle, L or D-isoleucyl, L or D-arginyl, L or D-tryptophanyl, L or D-tyrosyl, L or D-lysyl and L or D-ornithyl.

Reference is made to the following examples of radicals derived from a peptide formed from 2 to 5 amino acids and which can be used here: L or D-glutamyl-L or D-glutamyl-L or D-alanyl-L or D-tyrosylglycyle, L or D-alanyl-L or D-phenylalanyl-L or D-isoleucyl-glycyl, L or D-alanyl-L or D-tyrosylglycyl, L or D-lysylglycyl, L or D-tyrosyl-β-alanyl, L or D-tyrosyl-L or D-methionylglycyl, L or D-tyrosyl-L or D-threonylglycyl, L or D-tyrosyl(O-sulphate)-L or D-methionylglycyl and L or D-tyrosyl(O-sulphate)-L or D-threonylglycyl.

For example, A can represent the following radicals: pyroglutamyl, N-acetyl, N-benzoyl, N-t-butyloxycarbonyl, glycyl, N-benzoylglycyl, N-benzyloxycarbonylglycyl, β-alanyl, N-acetyl-β-alanyl, N-t-butyloxycarbonyl-β-alanyl, N-benzoyl-β-alanyl, N-benzyloxycarbonyl-β-alanyl, N-pivaloyl-β-alanyl, N-t-butyloxycarbonyl, L or D-alanyl, N-benzyloxycarbonyl-L or D-prolyl, N-t-butyloxycarbonyl-L or D-homocysteinyl, N-benzyl oxycarbonyl-L or D-valyl, N-benzyloxycarbonyl-L or D-phenylalanyl, N-acetyl-γ-aminobutyryle, N-α-benzyloxycarbonyl-L or D-lysyl, N-ε-benzyloxycarbonyl-L or D-lysyl, N-α-benzyloxycarbonyl-L or D-lysylglycyl, N-t-butyloxycarbonyl-L or D-alanyl-L or D-tyrosylglycyl, N-benzyloxycarbonyl-L or D-glutamyl-L or D-glutamyl-L or D-alanyl-L or D-tyrosylglycyl and N-t-butyloxycarbonyl-L or D-alanyl-L or D-phenylalanyl-L or D-isoleycylglycyl.

For example, X can in particular be histamine or a derivative thereof in accordance with formula:

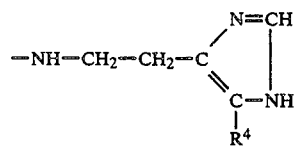

in which $R^4$ stands for hydrogen or $CH_3$.

X can also represent one of the following radicals:

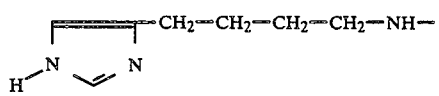

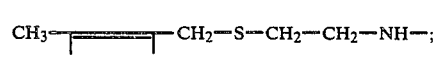

; and

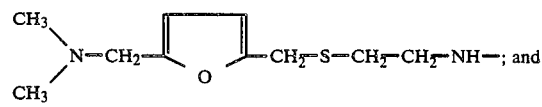

Preferably, according to the invention, B stands for the L-methionyl radical and X stands for a radical derived from histamine, such as the radical of formula:

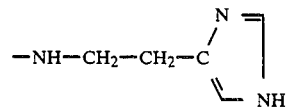

The presence of such a substituent in particular makes it possible to give the peptide derivative an antagonist effect, not only with respect to gastrin and related polypeptides, but also with respect to histamine in its action on the digestive tract.

According to a preferred embodiment, the peptide derivative according to the invention is in accordance with the following formula:

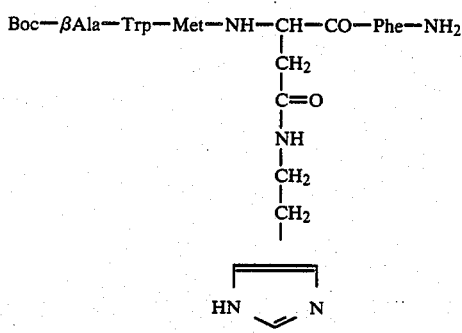

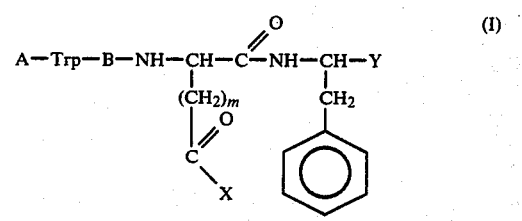

in which A, B, X, Y and m have the meanings given hereinbefore.

The peptide derivatives according to the invention can be used as a diagnostic agent or as a therapeutic agent. In particular, they are active in influencing gastric and pancreatic secretion, tonicity and gastric and intestinal motility.

The peptides according to the invention are also able to influence:
the transfer and secretion of water and electrolytes on the following organs: pancreas, liver, small intestine and Brunner's glands;
enzymatic secretion (stomach, pancreas, small intestine);
the absorption of glucose, electrolytes and water in the small intestine;
the smooth muscular system, e.g. on the organ stimulated by gastrin, such as the lower esophageal sphincter, stomach, small intestine, colon and vesicle, or on organs inhibited by gastrin, such as the pyloric sphincter, ileocecal sphincter and Oddi's sphincter;
the blood circulation of digestive organs, such as the stomach, small intestine and pancreas; and
the trophic action of the gastrin to a certain number of mucosas or organs, such as the gastric mucosa, the mucosa of the small intestine and the pancreas.

The peptide derivatives according to the invention can consequently be used as a therapeutic agent for the treatment of pathological states, such as the Zollinger Ellison syndrome, gastroduodenal ulcers in their typical and atypical forms and gastric hypersecretion of intestinal receptions.

Apart from the peptide derivative according to the invention, the pharmaceutical compositions may contain one or more diluents or excipients which are acceptable from the pharmaceutical standpoint and which are not toxic. It is also possible to add other active principles to the pharmaceutical composition. It is possible to obtain pharmaceutical compositions by using standard processes and standard excipients. Examples of suitable compositions are e.g. coated or uncoated tablets, capsules, aqueous suspensions or solutions, emulsions, aqueous or non-aqueous injectable suspensions or solutions, powders suitable for dispersion and depot composition. The aqueous solutions can also contain dimethylsulphoxide and/or sodium chloride.

The preferred compositions are sterile, injectable, aqueous, isotonic suspensions or solutions. Generally, in order to obtain the sought effects, the pharmaceutical composition is administered in such a way that the total dose of the active peptide derivative, administered on one or more occasions, is 1 to 200 nmol/kg/day.

The invention also relates to a process for the preparation of the aforementioned peptide derivative.

This process consists of reacting, in the presence of a catalyst, a compound of formula:

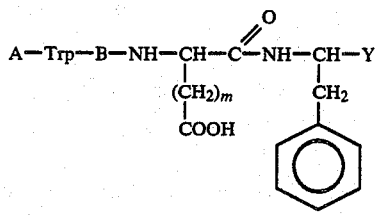

in which A, B, Y and m have the meanings given hereinbefore with a compound of formula H—X(IV), in which X has the meaning given hereinbefore, or one of its salts such as hydrochloric, acetate or trifluoroacetate.

The catalysts used have the function of preventing the cyclization of the residue to which group X will be attached. For example, use is made of 1-hydroxybenzotriazole or N-hydroxysuccinimide. For this reaction, it is conventional practice to dissolve the compound of formula (III) and the compound of formula (IB) in a solvent and to the reaction medium is also added a coupling agent, in order to permit the condensation of the carboxyl of compound (III) with compound (IV).

The solvents which can be used are the standard solvents used in peptide synthesis, such as dimethylformamide (DMF), dimethylsulphoxide (DMSO), ethyl acetate, water and their mixtures. In an aqueous medium, it is ensured that the pH remains between 5 and 7. If necessary, the pH is adjusted by the addition of an organic base, such as trimethylamine or N-methylmorpholine.

The coupling agents which can be used are those used conventionally in peptide synthesis, e.g. dicyclohexylcarbodiimide or 1-cyclohexyl-3-(2-morpholinoisoethyl)-carbodiimide (CMC). The pH of the reaction medium is preferably kept at 6 during the reaction, which can be brought about by the addition of an organic base, such as triethylamine.

The compounds of formulas (III) and (IV) used as starting products for the preparation of the peptides according to the invention can be prepared by conventional processes. The compound of formula (III) can e.g. be synthesized by the method of J. M. Davey, A. H. Laird and Y. S. Morley (J. Chem. Soc. C, 555, 1966).

The present invention also relates to a pharmaceutical composition, wherein it comprises as the active ingredient a peptide in accordance with the formula:

BRIEF DESCRIPTION OF THE DRAWINGS

Other features and advantages of the invention can be gathered from the following description of non-limitative embodiments with reference to the attached drawings, wherein show:

FIGS. 5, 6 and 7 graphs illustrating the inhibition of secretion plateaux stimulated by pentagastrin by injecting different doses of pentagastrin-histamine.

DETAILED DESCRIPTION OF THE INVENTION

EXAMPLE 1

Preparation of pentagastrin-histamine (PG-Hist).

(a) Preparation of pentagastrin: Boc-$\beta$Ala-Trp-Met-Asp-Phe-NH$_2$

Firstly, the hydrazide tripeptide (BOC-$\beta$Ala-Trp-Met-N$_2$H$_2$) is synthesized, followed by the dissolving of 780 mg (1.5 mmol) of this hydrazide tripeptide in 7 ml of dimethylformamide (DMF) and to the solution is added 1.5 mmol of NaNO$_2$ and 3 mmol of HCl at $-25°$ C., in order to convert the hydrazide tripeptide into azide. After stirring for 15 minutes at $-25°$ C., the solution is neutralized by adding 6 mmol of N-methylmorpholine. 1.5 mmol of amide dipeptide H-Asp-Phe-NH$_2$ dissolved in 6 ml of DMF and 1 ml of water is then added to the reaction medium. After stirring for 16 hours at $+4°$ C., the pentagastrin formed is precipitated by adding 200 ml of a 0.01N HCl solution at 0° C. After filtering and drying, the product is purified by triturations in ethyl acetate, followed by the recrystallization of the insoluble product in a mixture of 2-ethoxy-ethanol-water (1/10 by volume). This gives 770 mg (1 mmol) of pentagastrin (PG), whose analytical characteristics are identical to those of the pentagastrin marketed by Imperial Chemical Industries.

(b) Preparation of the pentagastrin-histamine derivative (PG-Hist) of formula (II).

Figure 1:
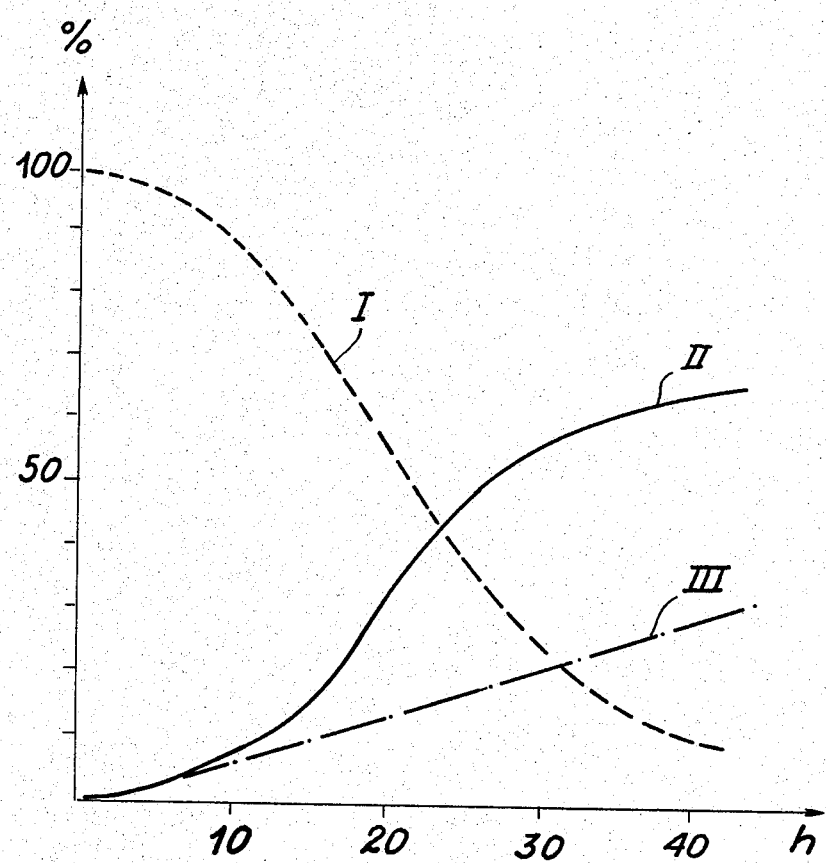
FIG. 1 a graph illustrating the kinetics of the pentagastrin-histamine derivative formation reaction, curve I representing the pentagastrin quantity (in molar %) as a function of the time (in h), curve II representing the quantity (in molar %) of the pentagastrin-histamine formed as a function of time (in h) and curve III illustrating the quantity (in molar %) of aminosuccinyl pentagastrin (Asc-PG) formed as a function of time (in h).

50 mg (65.1 $\mu$mol) of the previously obtained pentagastrin are dissolved in 0.3 ml of dimethyl formamide (DMF) and to this are added 11.8 mg (64.1 $\mu$mol-1 eq.PG) of histamine marketed by Sigma and 10 $\mu$l of an aqueous solution containing 18 $\mu$Ci of histamine $^{14}$C(U) obtained by the decarboxylation of $^{14}$C(U)-histidine, freshly purified (RAS=260 mCi/mmol) as a tracer. To the mixture is then added 12.7 mg (94 $\mu$mol, 1.45 equivalent of PG) of 1-hydroxybenzotriazole in 100 $\mu$l of DMF as the reaction catalyst, and 23.5 mg (114 $\mu$mol; 1.75 equivalent of PG) of dicyclohexylcarbodiimide as the coupling agent. The solution is cooled to 0° C. accompanied by magnetic stirring. The pH of the reaction mixture is then adjusted to 6 by triethylamine addition. The reaction is allowed to continue for 1 hour at 0° C. and then at ambient temperature. The advance of the reaction is followed analytically at 280 mm by thin layer chromatography (TLC) and by high performance liquid chromatography (HPLC). The formation kinetics of PG-Hist and Asc-PG are given in FIG. 1, whereof curves I, II and III illustrate the concentration variations (in molar %) of each compound: pentagastrin (PG/curve I), pentagastrin-histamine (PG-Hist/curve II) and pentagastrin aminosuccinyl (Asc-PG/curve III), as a function of time.

The reaction is at an end after about 40 hours. The dicyclohexylurea formed during the reaction (white solid) is then filtered on a Millipore LS filter (5 $\mu$m) and the pentagastrin-histamine is purified on a silica column 60 of length 28 cm and diameter 2.3 cm, whilst carrying out elution by a solvent gradient constituted by a mixture of ethyl acetate (AtoAc) and BAW (n-butanol/acetic acid/water with a volume ratio of 75/10/22), whose concentration varies between 100 EtoAc/0 BAW to 0 EtoAc/100 BAW at a flow rate of 4 ml/min, which makes it possible to successively elute the excess 1-hydroxybenzotriazole, the aminosuccinyl pentagastrin (Asc-PG) formed, the pentagastrin (PG) which has not reacted and then the PC-Hist$^{14}$C derivative (approximately 60% BAW). Each elution peak is analyzed by HPLC 14 C radioactivity counting and absorption spectrometry.

The thus obtained pentagastrin-histamine (PG-Hist) is not completely pure, so a second purification is carried out on a column containing gel LH20 (Sephadex) and having a length of 40 cm and a diameter of 2.5 cm, whilst using as the eluent the acetic acid/methanol/water mixture (1/1/1 by volume) at a flow rate of 0.5 ml/min. The fraction corresponding to the pentagastrin-histamine (PG-Hist) is eluted with 100 ml of solvent and lyophilized. In this way, 35.6 mg (41.4 $\mu$mol) of pentagastrin-histamine are obtained, i.e. an overall yield after purification of 63% of the starting pentagastrin.

The purity of the product is checked by HPLC, TLC, radio-recording and spectrography. For HPLC, use is made of Partisil 10-ODS-2 with different solvents and different elution programmes.

The following table 1 illustrates the results obtained by HPLC using a flow rate of 1.2 ml/min and the elution programmes P14, P15 and P16 of the following table 2. The products are detected by optical absorption at 280 nm, except in the case of histamine, where detection was effected at 215 nm.

TABLE 1

| Product | $T_R$ P.14 | $T_R$ P.15 | Retention time P.16 |
| --- | --- | --- | --- |
| PG | 17.03 | 15.70 | 15.85 |
| Histamine | | 2.86 | |
| 1-hydroxybenzotrizole | 6.76 | 5.40 | 2.90 |
| PG—histamine | 14.70 | 14.01 | 20.78 |
| BOC—Trp—Leu—Asl (Hist)Phe—NH$_2$ | | 14.50 | |

TABLE II

| Elution programme P.14 | Elution programme P.15 | Elution programme P.16 |
| --- | --- | --- |
| 0 min 100% A 0% B | 0 min 100% A 0% B | 0 min 100% C 0% D |
| 3 min 100% A 0% B | 3 min 100% A 0% B | 3 min 100% C 0% D |
| 23 min 0% A | 19 min 0% 100% B | 23 min 0% C |

TABLE II-continued

| Elution programme P.14 | Elution programme P.15 | Elution programme P.16 |
|---|---|---|
| 100% B | | 100% D |

In table 2, references A, B, C and D designate the following solvents:
A—acetonitrile/0.1M triethylamine phosphate buffer, pH 3.5, 20/80 (v/v)
B—80/20 (v/v)
C—acetonitrile/0.1N ammonium acetate, pH 4.7, 20/80 (v/v)
D—80/20 (v/v)

The following table 3 gives the results obtained by thin layer chromatography, performed on Si60-F254 plates for the product pentagastrin (PG), histamine (Hist), pentagastrin-histamine (PG-Hist) and the derivative BOC-Trp-Leu-Asp(Hist)-Phe-NH$_2$.

TABLE III

| Products | Rf of products | | | Development |
|---|---|---|---|---|
| | E | F | G | |
| Pentagastrin | 0.83 | 0.84 | 0.31 | IV,E,TMD |
| Histamine | 0 | 0 | 0 | N,TMD,R |
| PG—histamine | 0.30 | 0.41 | 0.42 | UV,E,TMD R |
| BOC—Trp—Leu—Asp—(Hist)—Phe—NH$_2$ | | 0.45 | | UV,E,TMD R |

In table 3, the references E, F and G designate the following solvents:
E=mixture of 20% ethyl acetate (EtOAC) and 80% of the mixture of n-butanol/acetic acid/water or BAW 75/10/22 (v/v/v)
F=100% BAW mixture
G=mixture of 60% EtOAC and 37% (v/v) of pyridine/acetic acid/water or PAW.

For this chromatography, the development of the plates was carried out by the conventional methods:
by ninhydrin (N),
by Ehrlich's reagent (E) (4-dimethylaminobenzaldehyde),
by the reagent TMD (4-4'-tetramethyldiaminodiphenylmethane) and/or
by radioactivity: R.

Figure 2:
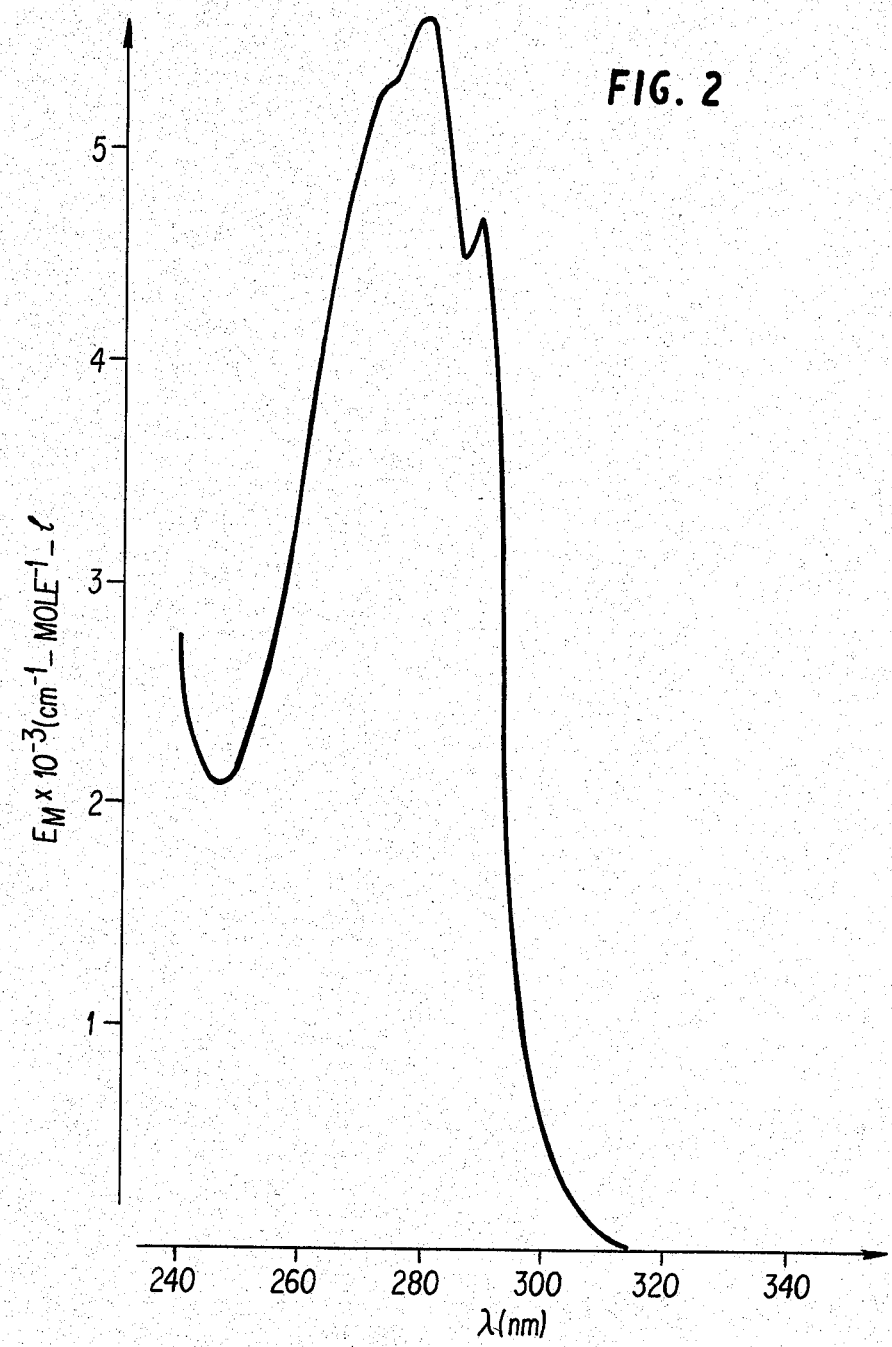
FIG. 2 the pentagastrin-histamine absorption spectrum.

FIG. 2 shows the absorption spectrum of pentagastrin-histamine.

Figure 3:
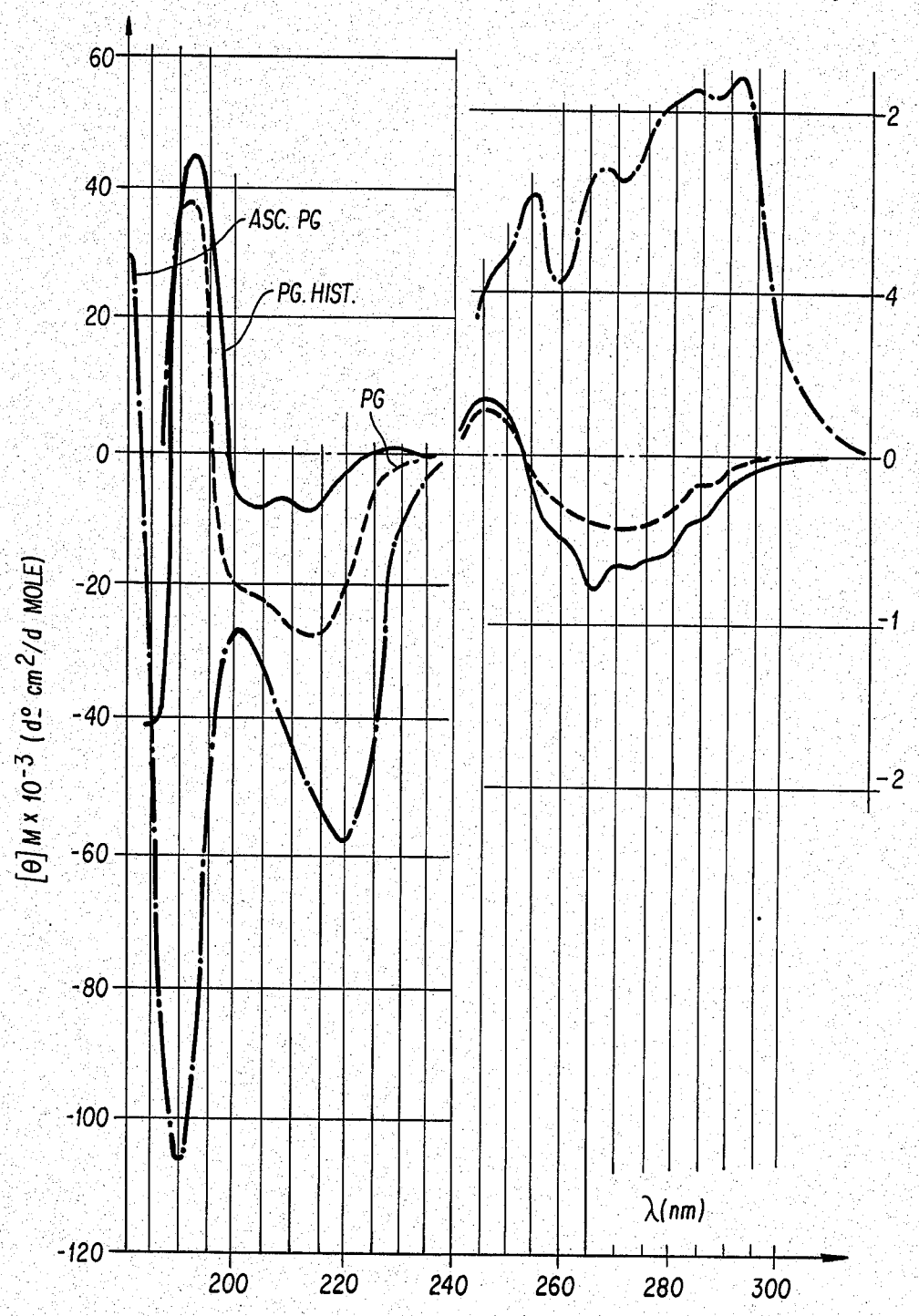
FIG. 3 the circular dichroism spectra of pentagastrin-histamine, pentagastrin and aminosuccinyl pentagastrin, in trifluoroethanol.

FIG. 3 shows the circular dichroism spectra of pentagastrin, pentagastrin-histamine and aminosuccinyl pentagastrin, dissolved in trifluoroethanol.

In the case of pentagastrin-histamine, the greater intensity of the dichroic signals in the aromatic region suggests a greater rigidity of tryptophan. In the remote ultraviolet, the amplitude of the positive band centered at 193 (contribution of the $\pi$-$\pi^*$ transitions of the peptide bonds and phenylalanine) is slightly higher in the case of pentagastrin-histamine, whereas at about 200 to 220 nm, the ellipticity of this compound is lower.

However, there is only slight difference in the general configuration of the two spectra (PG, PG-Hist), which shows a similarity in the overall formation of the two peptides.

EXAMPLE 2

In this example, the biological activity of the pentagastrin-histamine derivative obtained in example 1 is checked on the hydrochloric acid secretion, by using anesthesized rats with a perfused stomach, in accordance with the technique of Ghosh and Schild, modified by Lai (Bri.J.Parmac. 13, 54-61 1958 Nand Gut. 5, 327-333, 1964).

For the purpose of these tests, use was made of male Wistar rats weighing 300±25 g. The rats were not allowed to take solid food for 18 hours, but were allowed to drink water freely. They were then anesthesized with urethane (1.25 g/kg) by the intramuscular route. The temperature of the rats was maintained at 34° C. by means of lamps, approximately 60 cm away from them. A polyethylene catheter was introduced into the esophagus up to the level of the cardia and a second catheter for collecting the stomach secretion at the duodenum. After washing the stomach, the latter was continuously perfused with a 0.9% sodium chloride solution, at a flow rate of 1 ml/min, using a peristaltic pump connected to the catheter of the esophagus.

After a period of stabilizing the system lasting approximately 90 minutes after the operation, the compounds which it was wished to study were injected intravenously into the vein of the penis and the gastric secretion was collected by fractions taken every 20 minutes, the interval between these injections being min 90 minutes. The acidity of the sample fractions was dosed by means of a 0.01N sodium solution at the phenolphthalein colour change.

(A) First series of experiments: no agonist effect

The rats were injected with different doses of pentagastrin-histamine and the results obtained were compared with those obtained on injecting the same quantity of pentagastrin.

Figure 4:
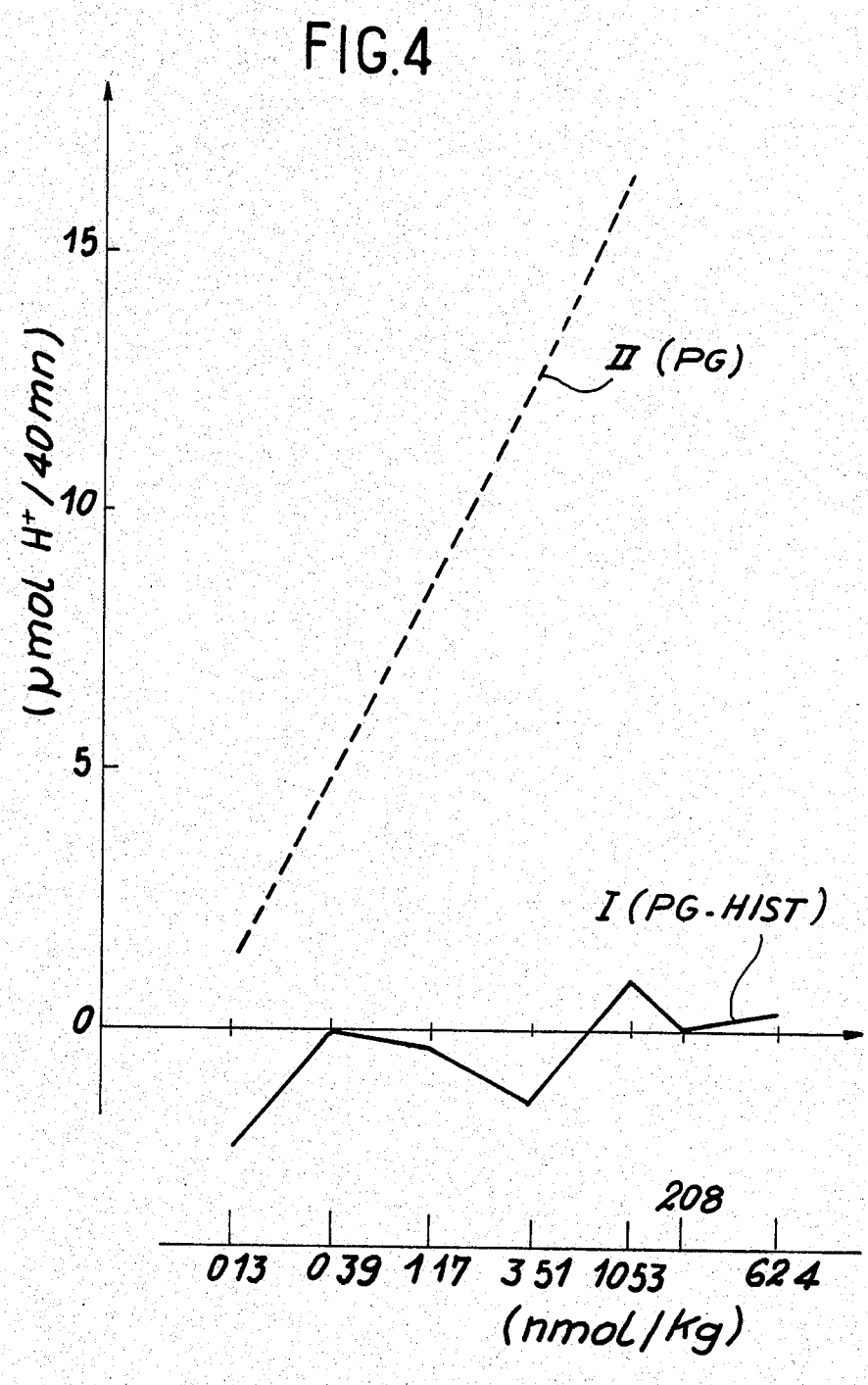
FIG. 4 the hydrochloric acid secretory response as a function of time and injected products (pentagastrin and pentagstrin-histamine), during tests performed on rats.

FIG. 4 illustrates the results obtained. On the abscissa are plotted the doses (in nmol/kg) of pentagastrin (PG) or pentagastrin-histamine (PG-Hist) injected and on the ordinate are plotted the acid quantities dosed in the collected fractions, expressed in $\mu$mol H$^+$/40 min. Curve I relates to pentagastrin-histamine (PG-Hist) and curve II to pentagastrin (PG). As can be seen, pentagastrin-histamine does not stimulate the hydrochloric acid secretion, even at a dosage of 62.4 nmol/kg, whilst the pentagastrin activity is maximum as from 20 nmol/kg.

Thus, the pentagastrin-histamine derivative has no agonist effect. Moreover, it can be concluded therefrom that the amide bond between the pentagastrin and the histamine is not cut off in vivo, because then the agonist activity of the released pentagastrin would be observed.

(B) Second series of experiments: antagonist property of the pentagastrin-histamine derivative relative to pentagastrin In these experiments, to rats distributed into groups was administered an intravenous perfusion of an isotonic solution containing pentagastrin in order to stimulate hydrochloric acid secretion. On the stimulated secretion becoming stable, i.e. after approximately 90 minutes perfusion, a pentagastrin-histamine dose was administered, whilst maintaining pentagastrin perfusion.

The results obtained are given in FIGS. 5 6 and 7, which show different inhibition curves of the secretion plateau often stimulated by pentagastrin perfusion at doses of 0.16, 1.3 and 5.2 nmol/kg/h. In these graphs, on the abscissa is plotted the time and on the ordinate the secretion plateau inhibition percentage.

The various curves of FIG. 5 (PG at 0.16 nmol/kg/h) relate to the inhibition obtained with a dose of 0.16 nmol/kg of pentagastrin-histamine (curve 1), with a dose of 0.64 nmol/kg of pentagastrin-histamine (curve 2), with a dose of 1.3 nmol/kg of pentagastrin-histamine (curve 3) and with a dose of 5.2 nmole/kg/ of PG-Hist (curve 4).

FIG. 6 shows the results obtained when the secretion plateau is obtained at a dose of 1.3 nmol/kg/h of pentagastrin. Curve 1 relates to the inhibition obtained by a pentagastrin-histamine dose of 1.3 nmol 3 kg and curve 2 to the inhibition obtained for a pentagastrin-histamine dose of 5.2 nmol/kg/h.

FIG. 7 illustrates the results obtained when the perfusion contains 5.2 nmol/kg/pentagastrin. Curve 1 relates to the inhibition obtained with a PG-Hist dose of 5. 2 nmol/kg and curve 2 to the inhibition obtained with a pentagastrin-histamine dose of 10.8 nmol/kg.

In the following table IV, the mean values (±ESM) of the maximum inhibition percentages obtained on a group of n rats are given.

The maximum inhibition (35 to 45%) is reached when the PG-Hist dose is 4 times higher than the pentagastrin dose. On further increasing the PG-Hist dose, the inhibition time is then extended and exceeds 3 h for PH-Hist doses of 5.2 nmol/kg and pentagastrin doses of 0.16 nmol/kg.

When administering the pentagastrin-histamine and the pentagastrin in the ratio of 1:1, the maximum inhibition of the secretion plateau varies from 15 to 25% and this inhibition lasts approximately 80 minutes. When the two compounds are in a PG-Hist/PG=4 ratio, the maximum inhibition of the secretion plateau reaches 35 to 45% and the inhibition time is then approximately 2 hours.

(C) Third series of experiments: antagonist property of pentagastrin-histamine to histamine In this case, use is made of the same operating procedure as in the second group of experiments, by stimulating the secretion by histamine. In this case, a higher histamine dose (13.5 μmol/kg/h) is injected. After the appearance of the secretion plateau, the pentagastrin histamine is injected at a rate of 150 nmol/kg or, for comparison purposes, 150 nmol/kg of cimetidine.

Cimetidine, which is in accordance with the formula:

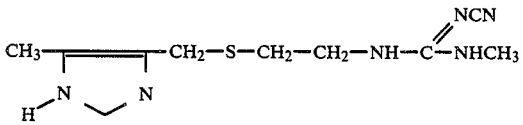

is a compound known for its antagonist activity to histamine.

Figure 8:
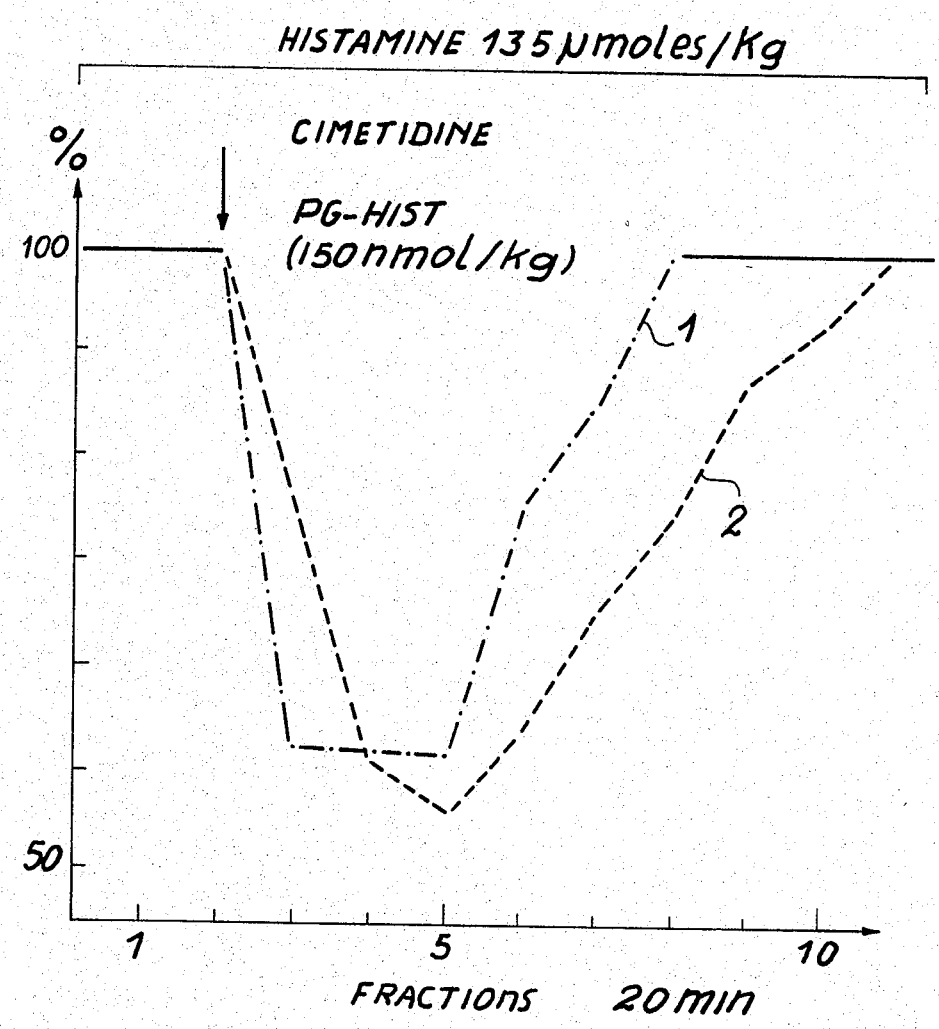
FIG. 8 a graph illustrating the inhibition of the secretion plateaux stimulated by histamine by means of pentagastrin-histamine or cimetidine.

FIG. 8 illustrates the results obtained. Curve 1 relates to the inhibition obtained with cimetidine and curve 2 to the inhibition obtained with pentagastrin-histamine.

It can be seen that the injection of the same dose of cimetidine and pentagastrin-histamine leads to an inhibition very close to the histamine response both as regards intensity (approximately 55% inhibition) and duration (approximately 3 h).

In these experiments, the mean value (±ESM) of the maximum inhibition percentages obtained is 56.5±7.2% on a group of 4 rats for pentagastrin-histamine (150 nmol/kg) and 54.4±2.7% on a group of 4 rats for cimetidine at the same dose of 150 nmole/kg.

TABLE IV

Mean values (± ESM) of the maximum inhibition percentages obtained on groups of n rats by injecting pentagastrin-histamine on different pentagastrin secretion plateaux.

| Injected PG-Hist doses nmole/kg | Pentagastrin doses (nmil/kg/h) in secretion plateaux | | |
|---|---|---|---|
| | 0.16 | 1.3 | 5.2 |
| 0.16 | 25.2 ± 2.3% n = 6 | | |
| 0.64 | 38.0 ± 1.7% n = 6 | | |
| 1.3 | 33.6 ± 7.6% n = 5 | 15.2 ± 6.3% n = 7 | |
| 5.2 | 32.3 ± 7.8% n = 11 | 46.0 ± 9.0% n = 5 | 14.1 ± 1.2% n = 6 |
| 20.8 | | | 35.2 ± 3.0% n = 9 |

What is claimed is:
1. A peptide derivative having the following formula:

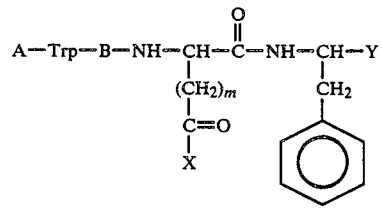

wherein A stands for hydrogen, a radical selected from the group of D or L-pyroglutamyl, L or D-alanyl, β-alanyl, glycyl, L or D-prolyl, L or D-valyl, L or D-phenylalanyl, L or D-homocysteyl, L or D-aspartyl, L or D-glutamyl, L or D-histidyl, L or D-methionyl, L or D-threonyl, L or D-seryl, L or D-cysteyl, L or D-leucyl, L or D-isoleucyl, L or D-arginyl, L or D-tryptophanyl, L or D-tyrosyl, L or D-lysyl and L or D-ornithyl, a group of the formula DE wherein D represents the N-t-butyloxy-carbonyl (BOC), tert-amyloxycarbonyl (tACO), N-benzyloxycarbonyl, N-benzoyl, N-acetyl, N-pivaloyl, N-carbamoyl or N-succinyl radical, and E stands for a single bond, a radical derived from an amino acid selected from the group of D or L-pyroglutamyl, L or D-alanyl, β-alanyl, glycyl, L or D-prolyl, L or D-valyl, L or D-phenylalanyl, L or D-homocysteyl, L or D-aspartyl, L or D-glutamyl, L or D-histidyl, L or D-methionyl, L or D-threonyl, L or D-seryl, L or D-cysteyl, L or D-leucyl, L or D-isoleucyl, L or D-arginyl, L or D-tryptophanyl, L or D-tyrosyl, L or D-lysyl and L or D-ornithyl, said amino acid being either unsubstituted or substituted by $HSO_3$, or a peptide having from 2 to 5 amino acids selected from the group of (L or D)-glutamyl-(L or D)-glutamyl-(L or D)-alanyl-(L or D)-tyrosylglycyl, (L or D)-alanyl-(L or D)-phenylalanyl-(L or D)-isoleucyl-glycyl, (L or D)-alanyl-(L or D)-tyrosylglycyl, (L or D)-lysylglycyl, (L or D)-tyrosyl-β-alanyl, (L or D)-tyrosyl-(L or D)-methionylglycyl, (L or D)-tyrosyl-(L or D)-threonylglycyl, (L or D)-tyrosyl (O-sulphate)-(L or D)-methionylglycyl and (L or D)-tyrosyl (O-sulphate)-(L or D)-threonylglycyl, said peptide being, either unsubstituted or substituted by $HSO_3$; B represents the L-methionyl, D-methionyl, L-norleucyl, D-norleucyl, L-leucyl, D-leucyl, L-norvalyl or D-norvalyl radical; Y represents H, $CH_2OH$, $COOR^1$ with $R^1$ representing hydrogen or an alkyl radical of $C_1$ to $C_4$ or $CO-NHR^2$ with $R^2$ representing hydrogen, an alkyl radical of $C_1$ to $C_4$ or $NH_2$; m is an integer between 0 and 6; and X represents a radical of formula:

$$-N(R^3)-(CH_2)_n-Z-(CH_2)_p-Q$$

in which n is an integer between 1 and 8, p is an integer between 0 and 3, $R^3$ stands for H or $CH_3$, Z stands for a single bond or S, and Q represents a radical selected from the radicals having the formula:

[imidazole ring with $R^4$ substituent]

in which $R^4$ stands for H or an alkyl radical of $C_1$ to $C_4$,

[oxazole with $R^5$]; [thiophene with $R^5$]; [furan with $R^5$]

with $R^5$ standing for H, an alkyl radical of $C_1$ to $C_4$, or $$(CH_3)_2N-R^6-$$

with $R^6$ representing an alkylene radical of $C_1$ to $C_3$; and

[thiazole with $R^7$]

with $R^7$ representing H, an alkyl radical of $C_1$ to $C_4$, $$(CH_3)_2N-R^6-$$

with $R^6$ having the above-described meaning or $$-N=C(NH_2)_2$$

2. A peptide derivative according to claim 1, wherein B represents the L-methionyl radical.

3. A peptide derivative according to claims 1 or 2, wherein X represents the radical:

$$-NH-CH_2-CH_2-C\begin{smallmatrix}N=C\\ \\C-NH\\|\\R^4\end{smallmatrix}$$

in which $R^4$ stands for hydrogen or $CH_3$.

4. A peptide derivative according to claim 1, wherein X stands for

[imidazole]—$CH_2-CH_2-CH_2-CH_2-NH-$.

5. A peptide derivative according to claim 1, wherein X stands for:

$CH_3$—[imidazole]—$CH_2-S-CH_2-CH_2-NH-$.

6. A peptide derivative according to claim 1, wherein X stands for:

$(CH_3)_2N-CH_2-$[furan]$-CH_2-S-CH_2-CH_2-NH-$.

7. A peptide derivative according to claim 1, wherein X stands for:

[thiazole]—$CH_2-S-CH_2-CH_2-NH-$
with $-N=C(NH_2)_2$ substituent

8. A peptide derivative according to claim 1 having the formula:

BOC—β-Ala—Trp—Met—NH—CH—CO—Phe—NH₂
                              |
                              CH₂
                              |
                              C=O
                              |
                              NH
                              |
                              CH₂
                              |
                              CH₂—[imidazole: HN—N]

9. A pharmaceutical composition for the treatment of Zollinger-Ellison syndrome, gastroduodenal ulcers and gastric hypersecretion, which comprises as the active ingredient a peptide derivative according to claim 1.

10. The pharmaceutical composition according to claim 9, wherein the peptide derivative has the formula:

BOC—β-Ala—Trp—Met—NH—CH—CO—Phe—NH₂
                              |
                              CH₂
                              |
                              C=O
                              |
                              NH
                              |
                              CH₂
                              |
                              CH₂—[imidazole: HN—N]

* * * * *